United States Patent [19]

Kaiser

[11] 4,004,028

[45] Jan. 18, 1977

[54] PHENOXYPROPANOLAMINES

[75] Inventor: Carl Kaiser, Haddon Heights, N.J.

[73] Assignee: SmithKline Corporation, Philadelphia, Pa.

[22] Filed: Aug. 6, 1975

[21] Appl. No.: 602,158

[52] U.S. Cl. .......................... 424/321; 260/556 A
[51] Int. Cl.² ..................................... A61K 31/18
[58] Field of Search ............... 424/321; 260/556 A

[56] References Cited

UNITED STATES PATENTS 3,661,917  5/1972  Kaiser et al. ................. 260/556 A
3,801,631  4/1974  Comer et al. ................. 260/556 A
3,852,468  12/1974 Howe et al. ...................... 424/321

Primary Examiner—Norman A. Drezin
Attorney, Agent, or Firm—Joseph A. Marlino; Richard D. Foggio; William H. Edgerton

[57] ABSTRACT

Phenoxypropanolamine derivatives are prepared. These compounds have β-adrenergic stimulant activity particularly as selective bronchodilators.

6 Claims, No Drawings

PHENOXYPROPANOLAMINES

This invention relates to novel phenoxypropanolamine derivatives which have useful pharmacodynamic activity. More specifically, the compounds of this invention have utility as β-adrenergic stimulants with relatively greater activity on respiratory smooth muscle than on cardiac muscle. Therefore these compounds have direct bronchodilator action with minimal cardiac stimulation as demonstrated in standard pharmacological test procedures.

Two in vitro test systems used for determining selective β-stimulant activity are: (1) effect on spontaneous tone of guinea pig tracheal chain preparations as a measure of β-stimulant (direct relaxant) effect on airway smooth muscle, and (2) effect on rate of spontaneously beating right atria of the guinea pig as a measure of β-stimulant effect on cardiac muscle. The compounds of this invention have selective bronchodilating properties since they are active in (1) above at a dose lower than is required in (2) above resulting in a positive separation ratio.

The compounds of this invention are represented by the following general structural formulas:

FORMULA I

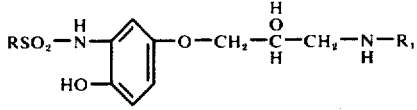

and

FORMULA II

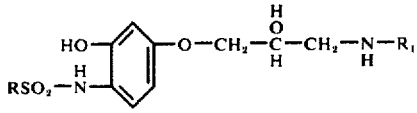

in which:
R represents lower alkyl of from 1 to 5 carbon atoms, straight or branched chain;
$R_1$ represents a branched chain lower alkyl group of from 3 to 5 carbon atoms, a cycloalkyl or cycloalkylmethyl group, the cycloalkyl moiety having from 3 to 6 carbon atoms, or

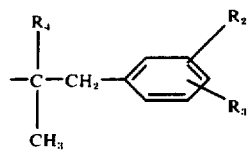

in which:
$R_2$ and $R_3$ represent hydrogen, hydroxy, methoxy or combined methylenedioxy; and
$R_4$ represents hydrogen or methyl.

Preferred compounds of this invention are represented by the above Formulas when R is methyl, and $R_1$ is isopropyl, t-butyl, cyclopropyl and cyclopentyl.

An advantageous compound of this invention is represented by Formula I and by 3-(4-hydroxy-3-methanesulfonamidophenoxy)-1-(tert-butylamino)-2-propanol which relaxes the spontaneous tone of guinea pig tracheal ring preparation at an $ED_{50}$ of 0.00219 mcg./ml. while increasing the rate of contraction of guinea pig right atria at an $ED_{25}$ of 0.409 mcg./ml. These activities give an absolute separation ratio of 186 which is a 372 fold improvement when compared to the corresponding activity of d, l-isoproterenol (absolute separation ratio = 0.5) in similar in vitro preparations.

The compounds of this invention may be used in the form of a pharmaceutically acceptable acid addition salt having the utility of the free base. Such salts, prepared by methods well known to the art, are formed with both inorganic or organic acids, for example: maleic, fumaric, benzoic, ascorbic, pamoic, succinic, bismethylenesalicylic, methanesulfonic, ethanedisulfonic, acetic, oxalic, propionic, tartaric, salicylic, citric, gluconic, aspartic, stearic, palmitic, itaconic, glycolic, p-aminobenzoic, glutamic, benzenesulfonic, hydrochloric, hydrobromic, sulfuric, cyclohexyl sulfamic, phosphoric and nitric acids.

Further the compounds of this invention contain at least one asymmetric carbon atom which is resolvable into d- and l- optical isomers. When $R_4$ in the above formulas is not methyl, another asymmetric carbon atom is formed and these compounds (diastereoisomers) may be resolved as d, l optical isomers. Unless otherwise specified in the description and accompanying claims, it is intended to include all isomers, whether separated or mixtures thereof.

Resolution of the optical isomers may be conveniently accomplished by fractional crystallization of their salts with optically active acids such as, for example, tartaric, camphor-10-sulfonic, 0,0-dibenzoyltartaric, 0,0-di(p-toluoyl)tartaric, camphoric, 2-pyrrolidone-5-carboxylic acids or N-acetylhyptophane from appropriate solvents.

The compounds of this invention are prepared as shown in the following sequence of reactions:

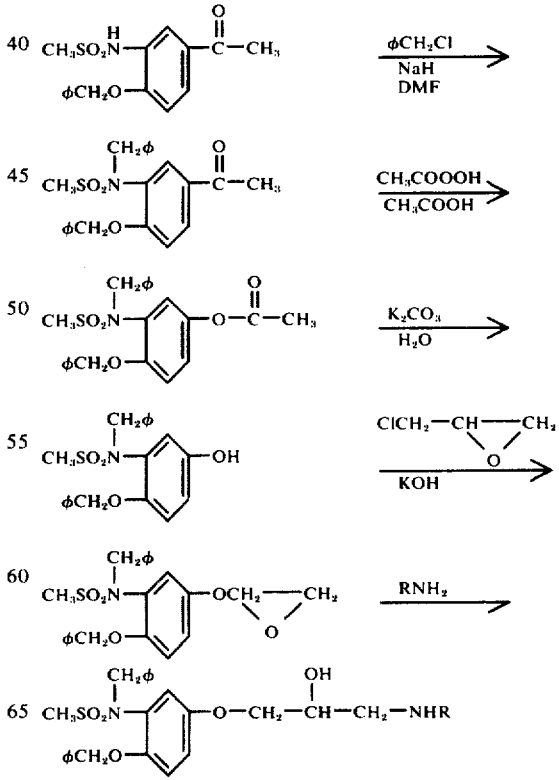

-continued

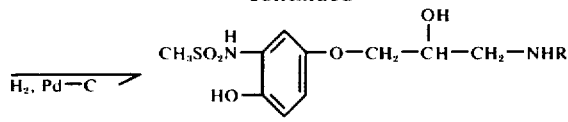

in which R is defined in Formula 1. Thus, as shown above, the appropriately substituted acetophenone is oxidized to give the corresponding phenyl acetate. The latter is then hydrolyzed and the resultant phenol is condensed with epichlorohydrin to yield an epoxide which upon treatment with the desired amine followed by catalytic hydrogenation, preferably with palladium-on-carbon, gives the desired phenoxypropanolamine product.

The starting materials used herein are either known or are prepared by methods well known in the art from readily available materials.

The compounds of this invention may be administered orally or parenterally in conventional dosage unit forms such as tablets, capsules, injectables or the like, by incorporating the appropriate dose of a compound of Formula 1, with carriers according to accepted pharmaceutical practices. Preferably a compound or an acid addition salt thereof is administered orally to an animal organism in a tablet or capsule comprising an amount sufficient to produce $\beta$-adrenergic stimulant activity. Eash dosage unit will contain the active ingredient in an amount of from about 1 mg. to about 40 mg., preferably from about 3 mg. to about 20 mg. Advantageously equal doses will be administered 2 to 4 times daily with the daily dosage regimen being from about 2 mg. to about 160 mg.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly the carrier or diluent can include any time delay material well known to the art, such as glyceryl monostearate or glyceryl distearate alone or with a wax.

A wide variety of pharmaceutical forms can be employed. Thus, if a solid carrier is used the preparation can be tableted, placed in a hard gelatin capsule in powder or pellet form, or in the form of a troche or lozenge. The amount of solid carrier will vary widely but preferably will be about 25 mg. to about 1 g. If a liquid carrier is used, the preparation will be in the form of a syrup, emulsion, soft gelatin capsule, sterile injectable liquid such as an ampul, or an aqueous or nonaqueous liquid suspension.

Of particular applicability is an aerosol dispensing system wherein the active medicament is incorporated with Freon (fluorohydrocarbon) or other inert propellant in an aerosol container. Such an aerosol system will deliver a metered dose, administered once or twice at a time as needed. Such an aerosol system will deliver a metered dose of about 100 mcg. to about 650 mcg.

The foregoing is a general description of how to prepare the compounds of this invention. The following examples illustrate the preparation of specific compounds having $\beta$-adrenergic stimulant activity. However, this should not be construed as a limitation of the invention since appropriate variations in the starting materials will produce other products set forth hereinabove.

EXAMPLE 1

To a stirred solution of 24.5 g. of 5-acetyl-2-benzyloxymethanesulfonanilide in 100 ml. of dimethylformamide is added 3.4 g. of a 57% dispersion of sodium hydride in mineral oil. The stirred mixture is heated at 70° for 15 minutes, cooled and a solution of 10.1 g. of benzyl chloride in 20 ml. of dimethylformamide is added dropwise. The mixture is stirred and heated at 85°-90° for 2 hours, cooled, diluted with ice water and then extracted with ethyl acetate. The solution is dried over magnesium sulfate and concentrated. Recrystallization of the residue from ethyl acetate-hexane gives 5-acetyl-N-benzyl-2-benzyloxymethanesulfonanilide.

To a solution of 6–9% peracetic acid in acetic acid, prepared by dropwise addition of 100 g. of 30% aqueous hydrogen peroxide solution to 450 g. of acetic anhydride at 35° (cooling required), is added 26.3 g. of 5-acetyl-N-benzyl-2-benzyloxymethanesulfonanilide and the solution is heated at 40° for 4 hours and stirred at 25° for 4 days. The mixture is poured into 750 ml. of water containing 2.0 g. of sodium thiosulfate and then filtered to give 5-acetoxy-N-benzyl-2-benzyloxymethanesulfonanilide.

To a stirred suspension of 14.1 g. of 5-acetoxy-N-benzyl-2-benzyloxymethanesulfonanilide in 100 ml. of methanol is added a solution of 6.3 g. of potassium carbonate in 100 ml. of water. The suspension is heated until solution is complete and the solution is stirred at 25° C. for 20 hours. The resulting mixture is concentrated in vacuo and the pH brought to 2 by addition of water and hydrochloric acid. The mixture is then extracted with ether and the extracts are dried and concentrated. The solid is recrystallized from ethyl acetate-hexane to yield N-benzyl-2-benzyloxy-5-hydroxymethanesulfonanilide.

A solution of N-benzyl-2-benzyloxy-5-hydroxymethane sulfonanilide (.01 mol), potassium hydroxide and epichlorohydrin (.03 mol) in ethanol (30 ml.) is stirred at 25° C. for 20 hours. The solution is concentrated in vacuo, the residue suspended in water and the mixture is extracted with ether. The extracts are dried and concentrated to yield 3-[4-benzyloxy-3-(N-benzyl-N-methanesulfonamido)phenoxy]-1,2-epoxypropane.

A solution of 3.5 g. of the above epoxypropane, 20 ml. of tert-butylamine and 50 ml. of methanol is stirred and refluxed for 6 hours and then concentrated in vacuo. The residue is placed in ethanol, the solution is acidified with ethereal hydrogen chloride and ether is added to give 3-(4-benzyloxy-3-(N-benzyl-N-methanesulfonamidophenoxy)-1-(tert-butylamino)-2-propanol hydrochloride having a melting point of 169°-171° C.

A mixture of the above propanol, 1.0 g. of 10% palladium-on-carbon and 100 ml. of methanol is hydrogenated on the Parr apparatus at ambient temperature, using an initial hydrogen pressure of 60 psi. After hydrogen uptake is completed, the reaction mixture is filtered and the filtrate is concentrated in vacuo. Recrystallization of the residue solid from methanol-ether gives 3-(4-hydroxy-3-methanesulfonamidophenoxy)-1-tert-butylamino-2-propanol hydrochloride, m.p. 145°-146° C.

EXAMPLE 2

Similarly, substituting 4-acetyl-2-benzyloxymethanesulfonanilide as a starting material and proceeding with the ensuing reactions as described above yields the corresponding 3-(3-hydroxy-4-methanesulfonamidophenoxy)-1-tert-butylamino)-2-propanol hydrochloride, m.p. 208°–210° C.

EXAMPLE 3

Following the procedure outlined in Example 1, and substituting the following amines for tertiary butyl amine:

Isopropylamine
Cyclopropylmethylamine
Cyclopentylamine
3,4,Dimethoxyphenylisopropylamine
Phenylisopropylamine
3,4,Methylenedioxyphenylisopropylamine the following products are respectively obtained:

3-(4-hydroxy-3-methanesulfonamidophenoxy)-1-isopropylamino-2-propanol
3-(4-hydroxy-3-methanesulfonamidophenoxy)-1-cyclopropylmethylamino-2-propanol
3-(4-hydroxy-3-methanesulfonamidophenoxy)-1-cyclopentylamino-2-propanol
3-(4-hydroxy-3-methanesulfonamidophenoxy)-1-(3,4-dimethoxyphenylisopropylamino)-2-propanol
3-(4-hydroxy-3methanesulfonamidophenoxy)-1-phenylisopropylamino-2-propanol
3-(4-hydroxy-3-methanesulfonamidophenoxy)-1-(3,4-methylenedioxyphenylisopropylamino)-2-propanol

EXAMPLE 4

Similarly, employing 5-acetyl-2-benzyloxyethanesulfonanilide and 5-acetyl-2-benzyloxybutanesulfonanilide as the starting materials respectively and continuing as described in Example 1 yields 3-(4-hydroxy-3-ethanesulfonamidophenoxy)-1-tert-butylamino-2-propanol and 3-(4-hydroxy-3-butanesulfonamidophenoxy)-1-tert-butylamino-2-propanol.

EXAMPLE 5

| Ingredients | Mg./Capsule |
|---|---|
| 3-(4-Hydroxy-3-methanesulfonamidophenoxy)-1-tert-butylamino)-2-propanol Hydrochloride | 5.0 mg. |
| Starch, U.S.P. | 50.0 mg. |
| Lactose, U.S.P. | 142.0 mg. |
| Magnesium Stearate, U.S.P. | 3.0 mg. |

The ingredienrs are thoroughly mixed and placed in a hard gelatin capsule. One capsule is taken three times a day.

What is claimed is:

1. A chemical compound of the formulas:

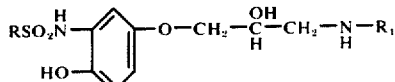

and

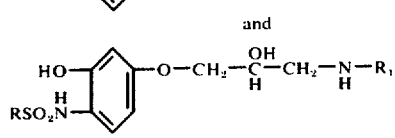

or a pharmaceutically acceptable acid addition salt of said compound, wherein:

R is a straight or branched chain lower alkyl of from 1 to 5 carbon atoms;

$R_1$ is branched chain lower alkyl of from 3 to 5 carbon atoms, cycloalkyl or cycloalkylmethyl, the cycloalkyl moiety having from 3 to 6 carbon atoms or

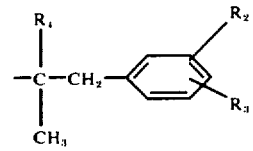

$R_2$ and $R_3$ are hydrogen, hydroxy, methoxy and $R_4$ is hydrogen or methyl.

2. A chemical compound according to claim 1 in which R is methyl.

3. A chemical compound according to claim 2 in which $R_1$ is tert-butyl being the compound 3-(4-hydroxy-3-methanesulfonamidophenoxy)-1-tert-butylamino)-2-propanol.

4. A chemical compound according to claim 3 in the form of a hydrochloride salt.

5. A pharmaceutical composition in dosage unit form having β-adrenergic stimulant activity comprising a pharmaceutical carrier and an effective amount of a chemical compound as defined in claim 1.

6. The method of producing β-adrenergic stimulant activity which comprises administering internally to animals requiring bronchodilation an amount sufficient to produce said activity a chemical compound as defined in claim 1.

* * * * *

UNITED STATES PATENT AND TRADEMARK OFFICE
CERTIFICATE OF CORRECTION

PATENT NO. : 4,004,028
DATED : January 18, 1977
INVENTOR(S) : Carl Kaiser

It is certified that error appears in the above—identified patent and that said Letters Patent are hereby corrected as shown below:

Column 6, formula appearing between lines 26 and 32, $R_1$ should be $R_4$.

Signed and Sealed this

Nineteenth Day of April 1977

[SEAL]

Attest:

RUTH C. MASON
*Attesting Officer*

C. MARSHALL DANN
*Commissioner of Patents and Trademarks*